United States Patent
Mac Clay

(12) 
(10) Patent No.: US 6,379,328 B1
(45) Date of Patent: Apr. 30, 2002

(54) DISPOSABLE SYRINGE

(76) Inventor: Fernando Horacio Mac Clay, 2000 Rosario, Santa Fe (AR)

( * ) Notice: Subject to any disclaimer, the term of this patent is extended or adjusted under 35 U.S.C. 154(b) by 0 days.

(21) Appl. No.: 09/351,060

(22) Filed: Jul. 9, 1999

(30) Foreign Application Priority Data

Apr. 15, 1999 (AR) ..................................... P 99 01 01741

(51) Int. Cl.⁷ .......................... A61M 37/00; A61M 5/00; A61M 5/315
(52) U.S. Cl. .......................... 604/82; 604/191; 604/226; 604/236
(58) Field of Search .............................. 604/82, 85, 89, 604/91, 92, 181, 183, 184, 187, 218, 226, 231, 232, 236, 191

(56) References Cited

U.S. PATENT DOCUMENTS

| | | | |
|---|---|---|---|
| 3,659,749 A | * | 5/1972 | Schwartz |
| 3,680,558 A | | 8/1972 | Kapelowitz ............ 128/218 M |
| 4,563,174 A | | 1/1986 | Dupont et al. ................ 604/89 |
| 5,704,918 A | | 1/1998 | Higashikawa ................ 604/191 |

FOREIGN PATENT DOCUMENTS

LU 88699 8/1996 .......... A61M/5/178

* cited by examiner

Primary Examiner—Michael J Hayes
(74) Attorney, Agent, or Firm—Mathews, Collins, Shepherd & Gould, P.A.

(57) ABSTRACT

The present invention is related with an improved syringe having a novel piston design. The syringe comprises an outer tube or cylinder made of, for example, plastic material, narrowed at its outlet for fitting a detachable hollow needle. Inside the outer tube the novel piston is slidable fitted including at its forward end a coupling defined by a coupling bolt and a retaining head which form part of the piston body. To the coupling a rubber bulb is rotatably fitted including a longitudinal hole for allowing fluids flow from tube to the needle and from the piston to the tube. The forward end of the piston includes an orifice defining fluid communication between the inner volume of the hollow piston and the inner volume of the tube. During the operation the piston can be rotated so as to align the hole of said rubber bulb and said orifice of the piston forward end for defining a fluid channel from the syringe to the hollow needle.

6 Claims, 3 Drawing Sheets

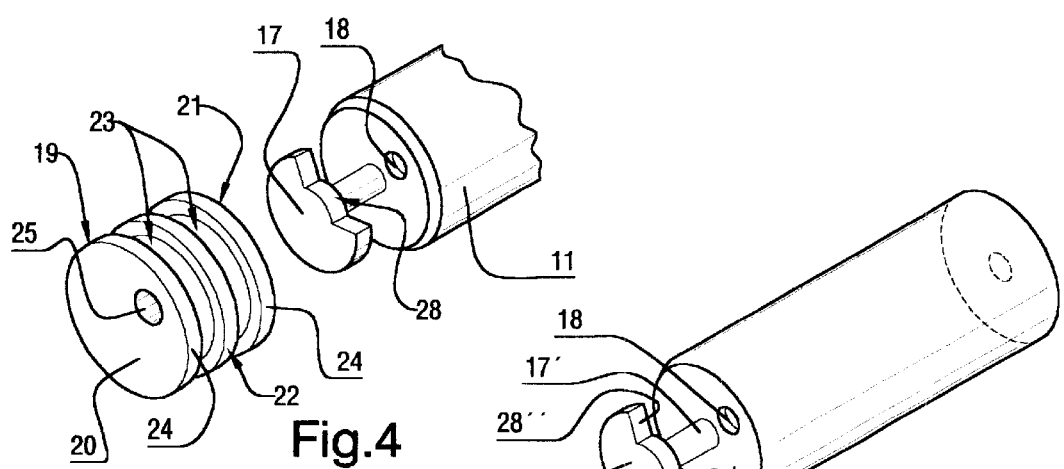
Fig.4
Fig.5
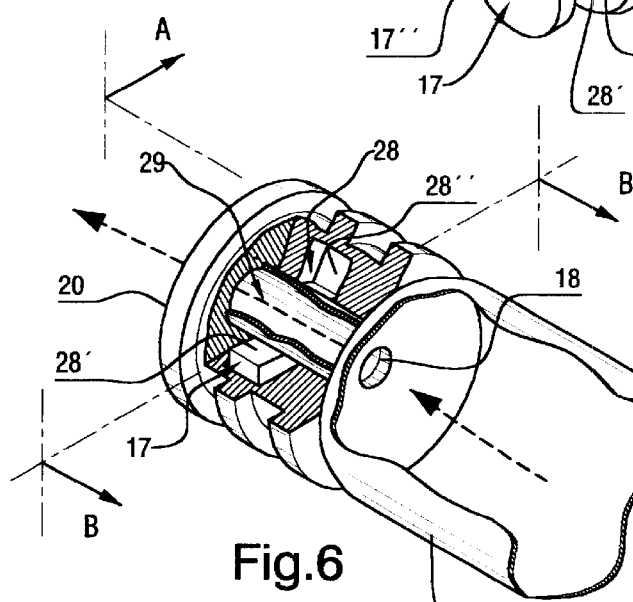
Fig.6
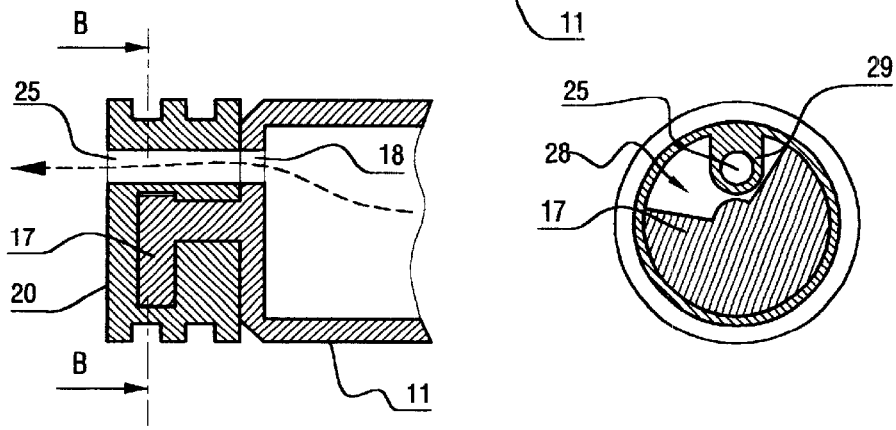
Fig.7
Fig.8

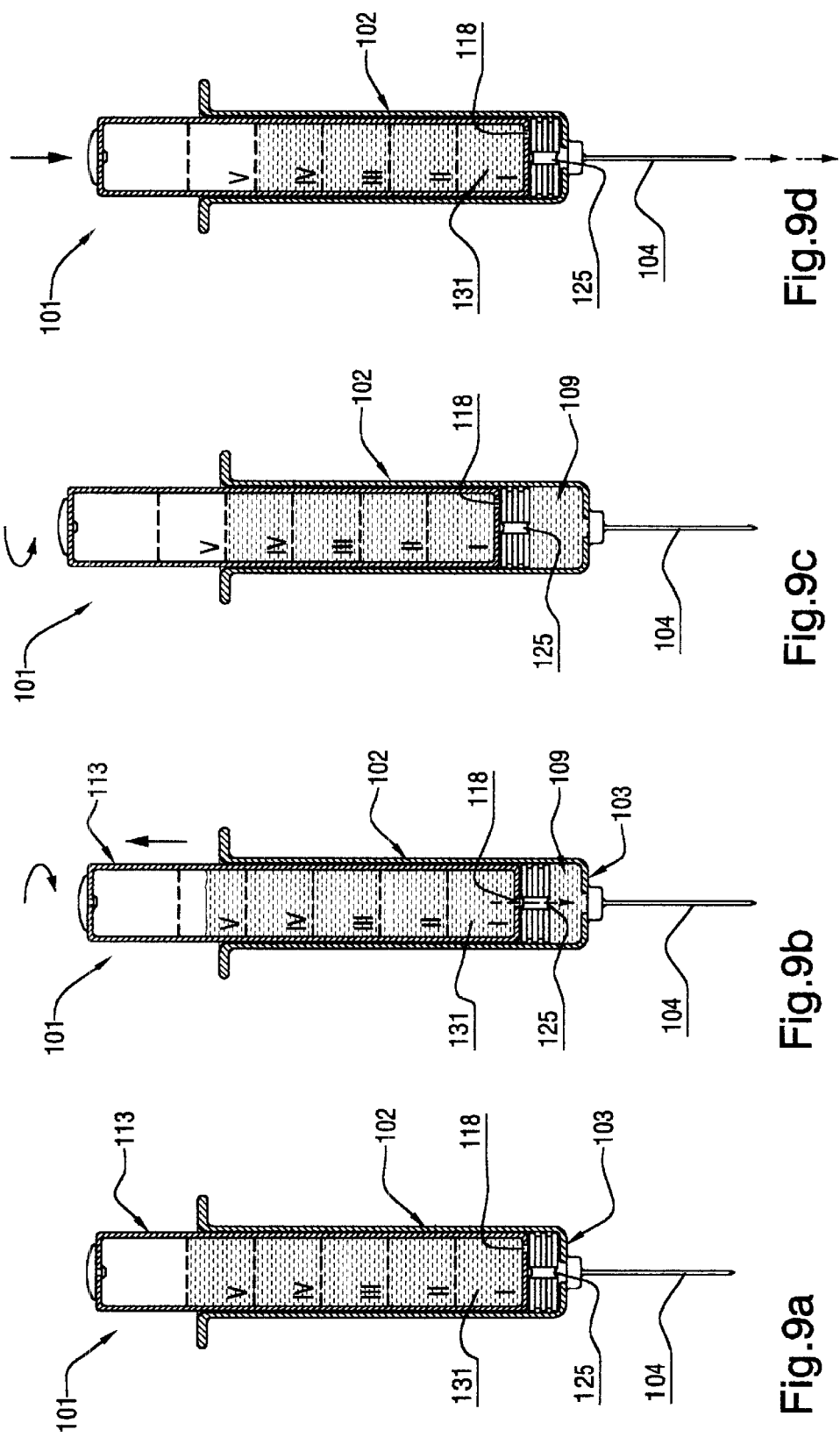

DISPOSABLE SYRINGE

BACKGROUND OF THE INVENTION

The present invention is related to improvements in syringes, and more particularly is referred to a novel disposable syringe.

There are thousands of different types of disposable syringes in the prior art. Most of these developments were created during the last years due to the proliferation of contagious diseases like AIDS. Handling syringes and blood for medical analysis is a potential risk of catching a mortal disease due to the growing number of people with AIDS. Therefore using disposable syringes was a useful way for decreasing the risk of contagion. Anyway, due to costs and budget shortfalls problems most hospitals were recycling disposable syringes. In order to avoid conflictive situations syringe manufacturers have developed a new type of disposable syringe including different kind of mechanisms through which the syringe can not be reused. That is, once the syringe is used for injecting a liquid, the piston can not be moved for charging the outer cylinder or tube again.

It is an object of the present invention a syringe with a novel piston which works as impelling means of drugs or diluents through a needle and at the same time as a ampoule for containing this liquid prior to be injected, as it will be explained in detail below.

Disposable syringes of the prior art basically comprises an outer tube or cylinder which may be made of plastic or glass material, narrowed at its outlet for fitting a detachable and hollow needle for injecting solutions into the body. Inside said outer cylinder or tube a piston with a rubber bulb in its end is slidable fitted comprising an elongated solid rod for drawing in a quantity of fluid. For example, this known syringe can be used for transferring a diluent from an ampoule to a flask containing a powder drug so as to form an solution to be injected to a patient. Thus, said tube-piston set works as an extracting-impelling means. This is specially useful when prior to inject a drug to a patient the nurse must mix a diluent contained in an ampoule with a powder contained in a flask. Therefore the syringe is used for transferring the diluent from the ampoule into the flask. Once the elements are mixed (powder-diluent) to the flask, the solution formed must be extracted with the same syringe for injecting it to the patient. Since these kind of ampoules usually include a rubber cap which must be bored with the needle tip during this transferring operation there is a potential risk of blunt this needle tip. If the needle tip is blunt the patient will surely feel pain and inconveniences during and after the injection.

Moreover, once diluent is injecting in to the flask containing a drug in a powder form the needle must be removed for shaking said flask for evenly mixing said diluent and powder, thus the needle must punch to a hole twice for extracting the final mixture of elements. This bothering operation takes time and in urgent and serious situations may lead to a negative and dangerous situation for the patient.

The above cited disadvantages are overcome with the syringe of the present invention. The purposed piston may contain all necessary means for immediately injecting a solution to a patient, as it may contain two different kind of elements (like a diluent and a powder drug) and in a few seconds these elements may be evenly mixed and injected as will be explained later.

SUMMARY OF THE INVENTION

It is an object of the present invention a novel syringe incorporating a new and improved piston. This syringe consist of an outer cylinder or tube for example made of plastic material (or any other suitable material without introducing unnecessary limitations to the invention), and narrowed at its outlet for fitting a detachable and hollow needle. Inside said tube or cylinder a piston with a rubber bulb in its end is slidable fitted. This piston comprises a hollow cylindrical body including one of its end a small hole defining a fluid passage between said piston and said tube. Said rubber bulb includes a longitudinal hole, defining this hole a fluid channel which may agree with the above cited hole for defining a liquid passage.

It is a further object of the present invention to provide a syringe whose hollow piston includes an outer end with a small orifice through which a liquid like a diluent may be loaded for readily carrying out a mixing operation of elements contained in the syringe as will be explained below.

It is a still further object of the invention to provide a novel syringe piston including coupling means for retaining said rubber bulb to the piston end, said retaining means capable of allowing the rotating movement of said piston in relation with said bulb.

The present invention is related with an improved and novel syringe which main novel feature resides on its piston design. The purposed syringe comprises an outer tube or cylinder made of, for example, plastic material, narrowed at its outlet for fitting a detachable hollow needle. Inside said outer tube the novel piston is slidable fitted including at its forward end coupling means defined by a coupling bolt and a retaining head which form part of the piston body. To said coupling means a rubber bulb is rotatably fitted including a longitudinal hole for allowing fluids flow from tube to the needle and from the piston to the tube. The forward end of said piston includes an orifice defining fluid communication between the inner volume of said hollow piston and the inner volume of said tube. During the operation the piston can be rotated so as to align said hole of said rubber bulb and said orifice of the piston forward end defining a fluid channel from the syringe to the hollow needle.

Summing up, the present invention is referred to a disposable syringe comprising a cylindrical tube with a forward end narrowed at its outlet including attaching means for fitting a detachable hollow needle, and this hollow cylindrical tube defines a rear opening through which a piston with a rubber bulb fitted in its end is fitted, wherein:

said piston comprises and elongated hollow body with a forward and rear end and capable of contained therein a liquid to be injected to a patient, said forward end includes a fluid communication orifice and coupling means in which said rubber bulb is rotatably fitted, said rubber bulb includes a longitudinal orifice and both coupling means and rubber bulb having restricting means capable of restricting piston rotating movement.

The term "polydose" as is used herein means a predetermined volume of a drug which must be administrated to a patient in multiple doses. That is, when a predetermined volume of drug must be injected to a patient but in multiple doses due to a specific medical treatment.

BRIEF DESCRIPTION OF DRAWINGS

FIG. 4 illustrates a perspective view of said rubber bulb including the above mentioned longitudinal hole, the forward end of said hollow piston with the coupling bolt the retaining FIG. 5 is a perspective view of the hollow cylindrical tube and coupling plug.

FIG. 6 is a cutaway perspective view of a rubber hollow bulb fitted with the coupling plug.

FIG. 7 is a A—A cross section view indicated in FIG. 6.

FIG. 8 is a B—B cross sectional view indicated in FIG. 7, finally:

FIGS. 9A–9D schematically show the purposed syringe but in accordance with an alternative embodiment of the present invention in which it could be used for polydoses applications.

DETAILED DESCRIPTION OF THE INVENTION

Figures 1, 2, 3:
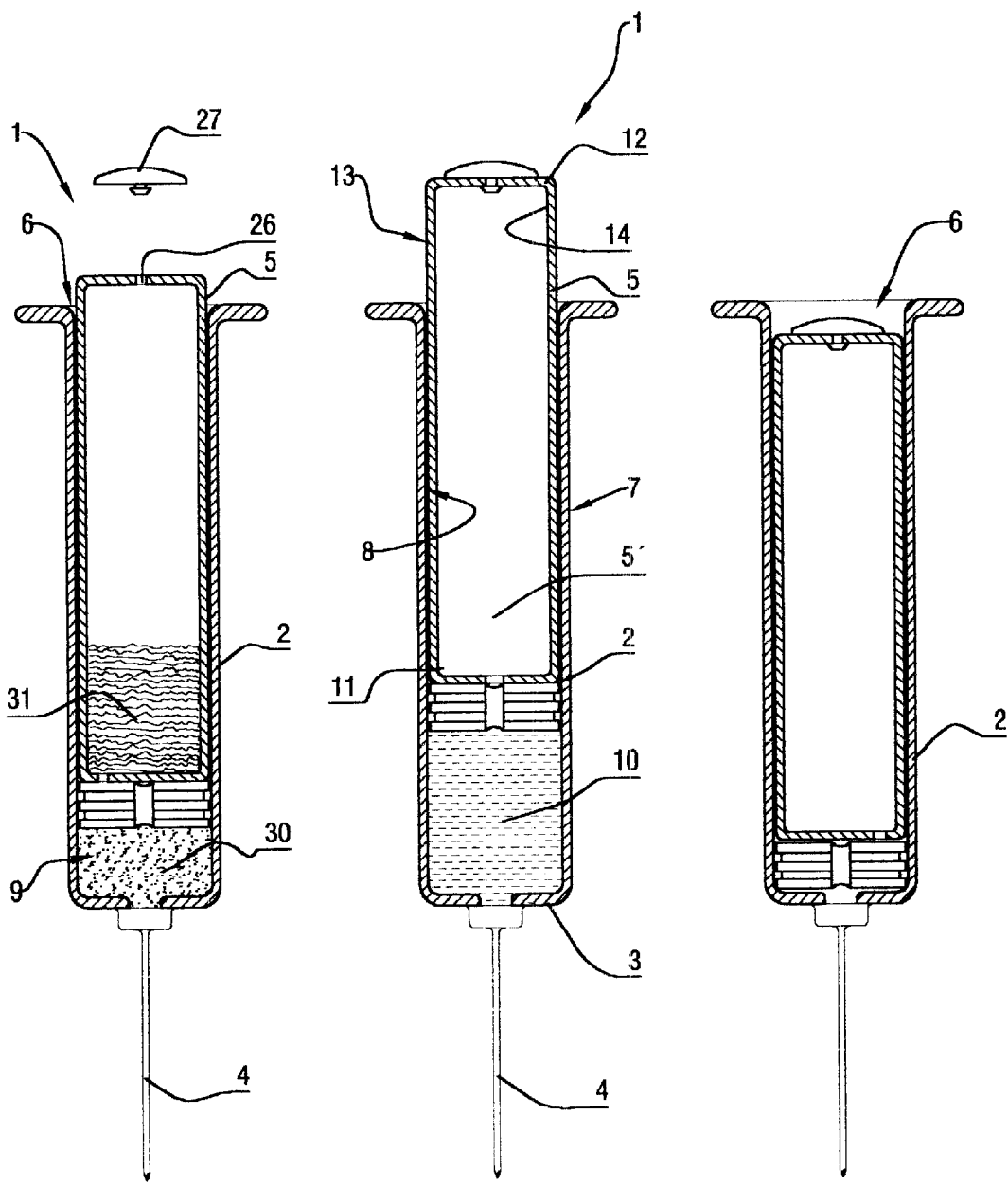
FIG. 1 shows a schematically cross sectional view of the purposed syringe in accordance with the present invention, ready to be used, illustrating the tube, hollow piston, a liquid inside said hollow piston (for example a diluent), and the needle fitted to the forward outer end of said tube. It can also be seen that the rear end of said hollow piston includes an orifice for filling said piston with a liquid to be injected, and said orifice is covered with a rubber plug (partially uncoupled)from the piston body for illustration purpose. The inner volume of this tube includes a drug to be mixed with the diluent contained in this piston. In the illustrated embodiment said drug is a freeze-dried powder.
FIG. 2 is another schematically cross sectional view like the former FIG. 1, in which the liquid contained in the hollow piston has passed to the tube by aligning the longitudinal hole of the rubber bulb and the piston forward end orifice.
FIG. 3 is a similar schematic cross sectional view of the purposed syringe once used. In this embodiment the piston is completely lodged inside the tube without any possibility of being taken out making the syringe useless.

The disposable syringe of this invention, generally indicated with reference 1, comprises as usual a cylindrical plastic tube or cylinder 2 whose forward end 3 is narrowed at its outlet including attaching means for fitting a detachable hollow needle 4 to be used for injecting, for example, solutions into a patient's body. Prior to be used this needle attaching means is normally capped with a rubber plug.

This hollow cylindrical tube 2 comprises an outer wall 7, an inner wall 8 and a rear opening 6 through which the cylindrical novel hollow piston 5 is inserted. As illustrated in FIGS. 1 and 2 before use half part of said piston 5 projects from the tube 2.

Into said piston 5 a predetermined mass of diluent 31 is changed (for example, serum) and inside said tube 2 a drug in the form of a freeze-dried powder 30 is changed (see FIG. 1).

This tube 2 defining a cylindrical inner volume 9 is capable of containing a mixture of the above cited elements 30–31, defining an injectable solution 10 as is illustrated in FIG. 2. Thus the syringe is ready to inject the fluid to a patient as will be explained below.

Said hollow cylindrical piston 5, involving the novel aspects of the present invention, comprises an elongated cylindrical body including a forward end 11, a rear end 12, outer side wall 13, and an inner side wall 15. Said forward end 11 comprising (see FIG. 5) a circular end wall 16 including a fluid orifice 18 and coupling projecting plug 17. Said coupling projecting plug 17 comprises a short cylindrical rod 17' ending in a retaining head 17".

As can be seen from FIG. 4, to said coupling plug 17 a rubber hollow bulb 19 is rotatably fitted. Said rubber bulb 19 comprises a substantially cylindrical siliconated rubber body with a front face 20, a rear face 21, and a lateral surface 22 including a longitudinal orifice 25 defining a passage between said front face and said rear face 20–21. The outer surface of this rubber bulb comprises three parallel arranged disk-like units 24. The arrangement of this orifice 18 is such that the user can rotate said piston 5 in relation with said rubber bulb 19 so as to align, in one of the possible arrangement of same, said hole 25 with said orifice 18 defining a fluid channel between the inner volume 5' of said piston 5 and the inner volume 9 of the above cited tube 2.

It should be noted that the above cited rotating operation of piston does not "drag" at the same time said of rubber bulb 19 since said rubber bulb 19 is tightly fitted against the inner wall 8 of said tube 2 and cannot be rotated once fitted.

As illustrated in said FIGS. 5–7, said retaining head 17" comprises a disk-like circular body with a cut or recess 28 interrupting the circular development of said head 17". Said recess defines a empty space between a left end edge 28' and a right end edge 28". The above cited orifice 18 is arranged in the front face 20 of said piston 5 so as to agree with the arrangement of said recess 28.

Into said rubber bulb 19 retaining head 17" is fitted so that there is no gap empty space between bulb and retaining head avoiding any fluid leak between them. Into said rubber bulb 19 and arranged so as to surround said longitudinal orifice 25 an internal rubber sleeve 29 (once the syringe is ready to be used) is arranged between said left end edge 28' and said right end edge 28" of retaining head 17, that is inside the above cited empty space created between said end edges. Said sleeve 29 working as limiting means of piston 5 forms an inner tube extending from face 20 to face 21 of said rubber bulb 19.

In order to fill in said hollow piston 5 with a liquid to be injected, rear end 12 includes an orifice 26 by which said liquid may be entered (it may also be filled this piston by aligning orifices 18–25 generating a charge via during manufacture of this syringe) which could be closed with a rubber plug 27. This plug is tightly fitted so as to maintain a total sterilization of diluent 31 inside said piston 5. Eventually for safety purposes this plug may be sealed by the manufacturer.

In accordance with the present invention, the disposable syringe 1 works as follows:

The purposed syringe 1 is specially useful for injecting a drug in the form of a freeze-dried powder to a patient which must be mixed with diluent prior to be injected. Both elements (diluent and drug) are already contained in the syringe for sale (FIG. 1). Thus the above cited inner volume 5' of piston 5 is filled in with diluent 31 and the inner volume 9 of tube 2 is filled in with a drug 30 in the form of a freeze-dried powder 30 (FIG. 1). Therefore prior to inject the liquid both diluent and drug must be mixed so as to form an injectable solution. In order to do that hole 25 and orifice 18 must be aligned by rotating said piston until said orifice 18 is arranged in alignment with said hole 25 creating a fluid passage from inner volume 5' to inner volume 9. In order to do that the piston is rotated so as run up said sleeve 29 against end edge 28". In this position orifices 18 and 25 coincide. If the piston is rotated in the opposite sense, that is once the sleeve run up against end edge 28", the orifice 18 will became closed and thus the liquid inside the piston 5 can not flow from the piston to the outer tube, remaining the syringe ready to be used. That is when the piston is arranged so as sleeve 29 rest on end edge 28' there is a fluid communication between piston 5 and tube 2, but when it rests on end edge 28" is ready to inject the solution to the patient. Once orifices 18–25 are aligned and the user (for example a nurse) pull the upper half of piston up a vacuum effect is created inside inner volume 9. Due to this vacuum effect diluent 31 contained inside piston 5 enters into the inner volume or chamber 9 forming a turbulence between said diluent 31 and freeze-dried drug 30 already lodged in said inner volume 9. Both elements are thus evenly mixed (FIG. 2) forming a solution to be injected but this must be complemented with an additional shaking for evenly mix powder and liquid, but the above cited turbulence allows a first mixture.

In order to carried out the injection operation, piston must be moved again in order to offset said orifice 18 and hole 25, thus said orifice 18 is closed by the rear face of rubber bulb thus 19 impelling fluid outwards through the hollow needle 4.

In the embodiment illustrated in the attached figures, once the injection operation is finished, piston 5 is completely lodged in tube 2, thus the syringe can not be reused defining the "unrecoverable and disposable" feature of the present invention.

Piston 5 can not be taken out from tube 2 since once the injection is done said piston is completely lodged inside it and can not be taken out.

The rotating movement of piston is limited by right and left end edges 28'–28" of retaining head 17". Since the above cited sleeve 29 remains between said right and left end edges 28'–28" said sleeve will work as a stopping means for limiting the rotating movement of said retaining head 17". Thus once said sleeve 29 rests on said end edge 28" the orifice 18 agrees with hole 25 and fluid pass through the passage form therebetween but when the user rotates piston 5 sleeve 29 rests on end edge 28' and the fluid passage is closed as was explained before.

Piston 5 is filled in with diluent through orifice 26, and this orifice is closed with a rubber plug 27 which defines a completely watertight closure for the diluent content of inner volume 5'.

Finally it should be noted that the purposed syringe is specially useful to be used for polydoses applications, that is when the same patient must receive a solution volume but fractionated in several injections. In this case several structural changes are made to the syringe without changing the inventive concept purposed. Reference to FIGS. 9A–9D will me made to describe this embodiment.

Making reference to FIG. 9A, syringe 101 is illustrated having a piston 105 longer than similar piston 5 illustrated and cited before. Since this piston 105 is longer than tube 102 it will never be completely lodged into said tube 102 as in the former case. Therefore the user can move this piston 105 without restrictions. In this figure syringe 101 contains a drug 110 to be injected to a patient, and in this embodiment no powder should be mixed with the liquid contained in this piston 105. As shown syringe 101 is ready to be used. In this particular case into inner volume 105' of said piston 105, 5 cm$^3$ of drug are contained to be injected to a patient in doses of 1 cm$^3$.

FIG. 9B shows the moment in which by rotating piston 105 orifices 118–125 coincide allowing the passage of, for example, 1 cm$^3$ from inner volume 105' of piston 105 to inner volume 109 of tube 102.

FIG. 9C shows how piston 105 is rotated so as to closed the fluid passage form by orifices 118–125.

Finally, FIG. 9D illustrates that inside piston 105 remains 4 cm$^3$ from the original 5 cm$^3$ of drug, and the remaining drug (1 cm$^3$) is lodged in tube 102 ready to be injected as was explained for the embodiment of FIGS. 1–8.

It should be noted that the polydoses embodiment does not change the original concept of the invention, because no changes are introduced to the piston 105, its rubber bulb 119 with the longitudinal orifice 125 defining a fluid passage between tube 102 and piston 105. Only the way of use and length of piston are changed.

This syringe could also be used for extracting human humors (blood, for example) and in this case the extraction sample would remain lodged inside piston 5 replacing test tubes usually used for containing this kind of biological samples.

I claim:

1. A disposable syringe comprising a hollow cylindrical tube with a forward end narrowed at its outlet including attaching means for fitting a detachable hollow needle, said hollow cylindrical tube defines a rear opening through which a piston with a rubber bulb fitted in its end is fitted;

said piston comprises an elongated hollow body with a forward and rear end capable of contained therein a liquid to be injected to a patient, said forward end includes a fluid communication orifice and coupling means in which said rubber bulb is rotatably fitted, said rubber bulb includes a longitudinal orifice and both coupling means and said rubber bulb having restricting means capable of restricting piston rotating movement wherein said rubber bulb includes an inner rubber sleeve surrounding its longitudinal orifice, said sleeve defines an inner tube extending from a front to a rear face of said rubber bulb.

2. The disposable syringe in accordance with claim 1 wherein said restricting means is defined by said inner sleeve.

3. A piston for a disposable syringe comprising an elongated hollow body containing therein a diluent to be mixed with a powder contained in a syringe outer cylinder or tube, a forward end includes a fluid communication orifice and coupling means comprising a retaining head with a disk-shaped body including a cut or recess which defines an empty space between a first end edge and a second end edge of said recess in which a rubber bulb is rotatably fitted, said rubber bulb includes a longitudinal orifice and both said coupling means and said rubber bulb having restricting means capable of restricting piston rotating movement of said piston, wherein said rubber bulb includes an inner rubber sleeve surrounding said longitudinal orifice, said sleeve defines an inner tube extending from a front to a rear face of said rubber bulb.

4. A piston for a disposable syringe in accordance with claim 3 wherein said restricting means is defined by said inner sleeve arranged between said first end edge and said second end edge of said recess.

5. A piston for a disposable syringe in accordance with claim 4, wherein a diluent is lodged in said piston capable to be mixed with a freeze-dried powder received in said tube or cylinder.

6. A piston for a disposable syringe in accordance with claim 4, wherein a drug in a form of a freeze-dried powder is contained in said tube and said piston is empty ready to be filled in with a diluent by a small orifice of its rear end, this said orifice may can be closed with a rubber plug.

* * * * *